US00PP31438P2

(12) United States Plant Patent
Verduin

(10) Patent No.: US PP31,438 P2
(45) Date of Patent: Feb. 11, 2020

(54) ***ASTILBE* PLANT NAMED 'HEAVY METAL'**

(50) Latin Name: *Astilbe arendsii*
Varietal Denomination: Heavy Metal

(71) Applicant: Harrie Verduin, Heemskerk (NL)

(72) Inventor: Harrie Verduin, Heemskerk (NL)

( * ) Notice: Subject to any disclaimer, the term of this patent is extended or adjusted under 35 U.S.C. 154(b) by 0 days.

(21) Appl. No.: 16/350,788

(22) Filed: Jan. 12, 2019

(51) Int. Cl.
*A01H 5/02* (2018.01)
*A01H 6/80* (2018.01)

(52) U.S. Cl.
USPC ..... Plt./407

(58) Field of Classification Search
USPC ..... Plt./407
See application file for complete search history.

*Primary Examiner* — Susan McCormick Ewoldt
(74) *Attorney, Agent, or Firm* — C. A. Whealy

(57) ABSTRACT

A new and distinct cultivar of *Astilbe* plant named 'Heavy Metal', characterized by its broadly upright and mounding plant habit; moderately vigorous growth habit; dark green-colored leaves; freely and uniformly flowering habit; red purple-colored flowers on upright and strong peduncles; and good container and garden performance.

2 Drawing Sheets

Botanical designation: *Astilbe arendsii.*
Cultivar denomination: 'HEAVY METAL'.

BACKGROUND OF THE INVENTION

The present invention relates to a new and distinct cultivar of *Astilbe*, botanically known as *Astilbe arendsii* and hereinafter referred to by the name 'Heavy Metal'.

The new *Astilbe* plant is a product of a planned breeding program conducted by the Inventor in Heemskerk, The Netherlands. The objective of the breeding program was to create new uniform and freely flowering *Astilbe* plants with attractive leaf and flower coloration.

The new *Astilbe* plant originated from an open-pollination in 2008 in Heemskerk, The Netherlands, of *Astilbe arendsii* 'Rhythm and Blues', disclosed in U.S. Plant Pat. No. 14,846, as the female, or seed, parent with an unknown *Astilbe arendsii* seedling selection as the male, or pollen, parent. The new *Astilbe* plant was discovered and selected by the Inventor as a single flowering plant from within the progeny of the stated open-pollination in a controlled greenhouse environment in Heemskerk, The Netherlands during the summer of 2010.

Asexual reproduction of the new *Astilbe* plant by vegetative divisions in a controlled nursery environment in Heemskerk, The Netherlands since December, 2010, has shown that the unique features of this new *Astilbe* plant are stable and reproduced true to type in successive generations.

SUMMARY OF THE INVENTION

Plants of the new *Astilbe* have not been observed under all possible combinations of environmental conditions and cultural practices. The phenotype may vary somewhat with variations in environmental conditions such as temperature and light intensity without, however, any variance in genotype.

The following traits have been repeatedly observed and are determined to be the unique characteristics of 'Heavy Metal'. These characteristics in combination distinguish 'Heavy Metal' as a new and distinct *Astilbe* plant:

1. Broadly upright and mounding plant habit.
2. Moderately vigorous growth habit.
3. Dark green-colored leaves.
4. Freely and uniformly flowering habit.
5. Red purple-colored flowers on upright and strong peduncles.
6. Good container and garden performance.

Plants of the new *Astilbe* differ primarily from plants of the female parent, 'Rhythm and Blues', in the following characteristics:

1. Inflorescences of plants of the new *Astilbe* are more compact than inflorescences of plants of 'Rhythm and Blues'.
2. Flowers of plants of the new *Astilbe* are red purple in color whereas flowers of plants of 'Rhythm and Blues' are lighter red purple in color.

Plants of the new *Astilbe* can be compared to plants of *Astilbe japonica* 'Montgomery', not patented. In side-by-side comparisons, plants of the new *Astilbe* and 'Montgomery' differ in the following characteristics:

1. Plants of the new *Astilbe* are more freely flowering than plants of 'Montgomery'.
2. Inflorescences of plants of the new *Astilbe* are broader than inflorescences of plants of 'Montgomery'.
3. Flowers of plants of the new *Astilbe* are red purple in color whereas flowers of plants of 'Montgomery' are dark red in color.

BRIEF DESCRIPTION OF THE PHOTOGRAPHS

The accompanying colored photographs illustrate the overall appearance of the new *Astilbe* plant showing the colors as true as it is reasonably possible to obtain in colored reproductions of this type. Colors in the photographs may differ slightly from the color values cited in the detailed botanical description which accurately describe the colors of the new *Astilbe* plant.

The photograph on the first sheet is a side perspective view of a typical flowering plant of 'Heavy Metal' grown in a container.

The photograph on the second sheet is a close-up view of typical inflorescences of 'Heavy Metal'.

DETAILED BOTANICAL DESCRIPTION

The aforementioned photographs and following observations, measurements and values describe plants grown during the summer in 17-cm containers in an outdoor nursery in Heemskerk, The Netherlands and under cultural practices typical of commercial *Astilbe* production. During the production of the plants, day temperatures ranged from 25° C. to 30° C. and night temperatures ranged from 15° C. to 20° C. Plants were one year old when the photographs and description were taken. In the following description, color references are made to The Royal Horticultural Society Colour Chart, 2015 Edition, except where general terms of ordinary dictionary significance are used.

Botanical classification: *Astilbe arendsii* 'Heavy Metal'.

Parentage:

*Female, or seed, parent.*—*Astilbe arendsii* 'Rhythm and Blues', not patented.

*Male, or pollen, parent.*—Unknown *Astilbe arendsii* seedling selection, not patented.

Propagation:

*Type.*—By vegetative divisions.

*Time to initiate roots.*—About three weeks at temperatures about 20° C.

*Root description.*—Thick, fleshy; typically brown in color, actual color of the roots is dependent on substrate composition, water quality, fertilizer type and formulation.

*Rooting habit.*—Freely branching; dense.

Plant description:

*Plant form and growth habit.*—Herbaceous perennial; broadly upright and mounding plant form with inflorescences held above the foliar plane; flowering stems and leaves basal; freely flowering with numerous basal branches developing per plant, dense and bushy; moderately vigorous growth habit; and freely and uniformly flowering habit.

*Growth rate.*—Moderately rapid to rapid; from divisions, about six months are required to produce fully-grown flowering plants in containers.

*Plant height* (*soil level to top of foliar plane*).—About 28.7 cm.

*Plant height* (*soil level to top of inflorescences*).—About 58.3 cm.

*Plant width* (*spread*).—About 50 cm.

*Stem description.*—Length: About 23.2 cm. Diameter: About 3.5 mm. Internode length: About 8.5 cm. Strength: Strong. Aspect: Erect to about 10° from vertical. Texture and luster: Moderately pubescent; moderately glossy. Color, developing: Close to 144A. Color, developed: Close to between 144A and 146D.

Leaf description:

*Arrangement.*—Alternate; biternately compound; on average, about 17 leaflets per leaf.

*Leaf length* (*excluding petiole*).—About 17 cm.

*Leaf width.*—About 17.6 cm.

*Terminal leaflet length.*—About 6 cm.

*Terminal leaflet width.*—About 3.8 cm.

*Lateral leaflet length.*—About 4.6 cm.

*Lateral leaflet width.*—About 3.1 cm.

*Leaflet shape.*—Ovate to close to rhomboidal.

*Leaflet apex.*—Apiculate.

*Leaflet base.*—Attenuate.

*Leaflet margin.*—Biserrate.

*Leaflet texture and luster, upper and lower surfaces.*—Moderately to densely pubescent; slightly rugose; slightly glossy.

*Leaflet venation pattern.*—Pinnate.

*Leaflet color.*—Developing leaflets, upper surface: Close to 143A. Developing leaflets, lower surface: Close to 146B. Fully expanded leaflets, upper surface: Darker than between NN137A and 147B; venation, close to 144A. Fully expanded leaflets, lower surface: Close to 147A to 147B; venation, close to 144B.

*Leaf petiole length.*—About 17.6 cm.

*Leaf petiole diameter.*—About 2.5 cm.

*Leaf and leaflet petiole strength.*—Strong.

*Leaf and leaflet petiole texture and luster, upper and lower surfaces.*—Moderately pubescent; glossy.

*Leaf and leaflet petiole color, upper surface.*—Close to 146A; proximally tinged with close to 178A.

*Leaf and leaflet petiole color, lower surface.*—Close to 144A; proximally, closer to 147C.

Flower description:

*Flower type and flowering habit.*—Single rotate flowers arranged on terminal compound panicles; flowers face upright, outward or downward depending on position on the inflorescence; panicles conical in shape; freely and uniformly flowering habit with about 1,500 flowers developing per inflorescence.

*Fragrance.*—Faint; sweet and pleasant.

*Natural flowering season.*—Plants begin flowering about 13 weeks after planting; continuously flowering from late spring until late summer in The Netherlands.

*Postproduction longevity.*—Flowers last about ten days on the plant; flowers not persistent.

*Flower buds.*—Height: About 4 mm. Diameter: About 2.5 mm. Shape: Ovate. Texture and luster: Smooth, glabrous; matte. Color: Close to 58A fading towards the base to close to 53C.

*Inflorescence height.*—About 21.1 cm.

*Inflorescence diameter.*—About 18 cm.

*Flower diameter.*—About 1.5 cm.

*Flower depth.*—About 9 mm.

*Petals.*—Quantity per flower: Typically five in a single whorl. Length: About 7.5 mm. Width: About 7.5 mm. Shape: Oblanceolate. Apex: Bluntly acute. Base: Narrowly cuneate. Margin: Entire. Texture and luster, upper and lower surfaces: Smooth, glabrous; matte. Color: Developing petals, upper and lower surfaces: Close to 61B. Fully expanded petals, upper and lower surfaces: Close to NN66C; color becoming closer to 70B with development.

*Sepals.*—Quantity per flower: Typically five in a single whorl, fused towards the base forming a campanulate-shaped calyx. Length: About 2.5 mm. Width: About 1.25 mm. Shape: Broadly ovate. Apex: Acute. Base: Cuneate, fused. Margin: Entire. Texture and luster, upper and lower surfaces: Smooth, glabrous; matte. Color: Developing sepals, upper and lower surfaces: Close to 155D; distally, tinged with close to 53B. Fully expanded sepals, upper and lower surfaces: Close to 145C; distally, tinged with close to 53C.

*Peduncles*.—Length: About 28.6 cm. Diameter: About 3 mm. Angle: Mostly erect. Strength: Strong. Texture and luster: Densely pubescent; matte. Color: Close to 146C tinged with close to 176A.

*Pedicels*.—Length: About 1.5 mm. Diameter: About 0.75 mm. Angle: About 40° from peduncle axis. Strength: Moderately strong. Texture and luster: Moderately to densely pubescent; matte. Color: Close to 53D.

*Reproductive organs*.—Stamens: Quantity per flower: Typically ten; anthers basifixed. Filament length: About 3 mm. Filament color: Close to 64D. Anther shape: Broadly ovate. Anther length: About 0.3 mm. Anther diameter: About 0.3 mm. Anther color: Close to 61A. Pollen amount: Moderate. Pollen color: Close to 156D. Pistils: Quantity per flower: Two. Pistil length: About 3 mm. Stigma diameter: About 0.1 mm. Stigma shape: Club-shaped. Stigma color: Close to 64B. Style length: About 2.75 mm. Style color: Close to 64C. Ovary color: Close to 64C.

*Seeds and fruits*.—To date, seed and fruit development have not been observed on plants of the new *Astilbe*.

Pathogen & pest resistance: To date, plants of the new *Astilbe* have not been noted to be resistant to pathogens and pests common to *Astilbe* plants.

Garden performance: Plants of the new *Astilbe* have been observed to have good garden performance and tolerate rain, wind and high temperatures of about 35° C. Additionally, plants of the new *Astilbe* have been observed to be suitable for USDA Hardiness Zones 5 through 10.

It is claimed:

1. A new and distinct *Astilbe* plant named 'Heavy Metal' as illustrated and described.

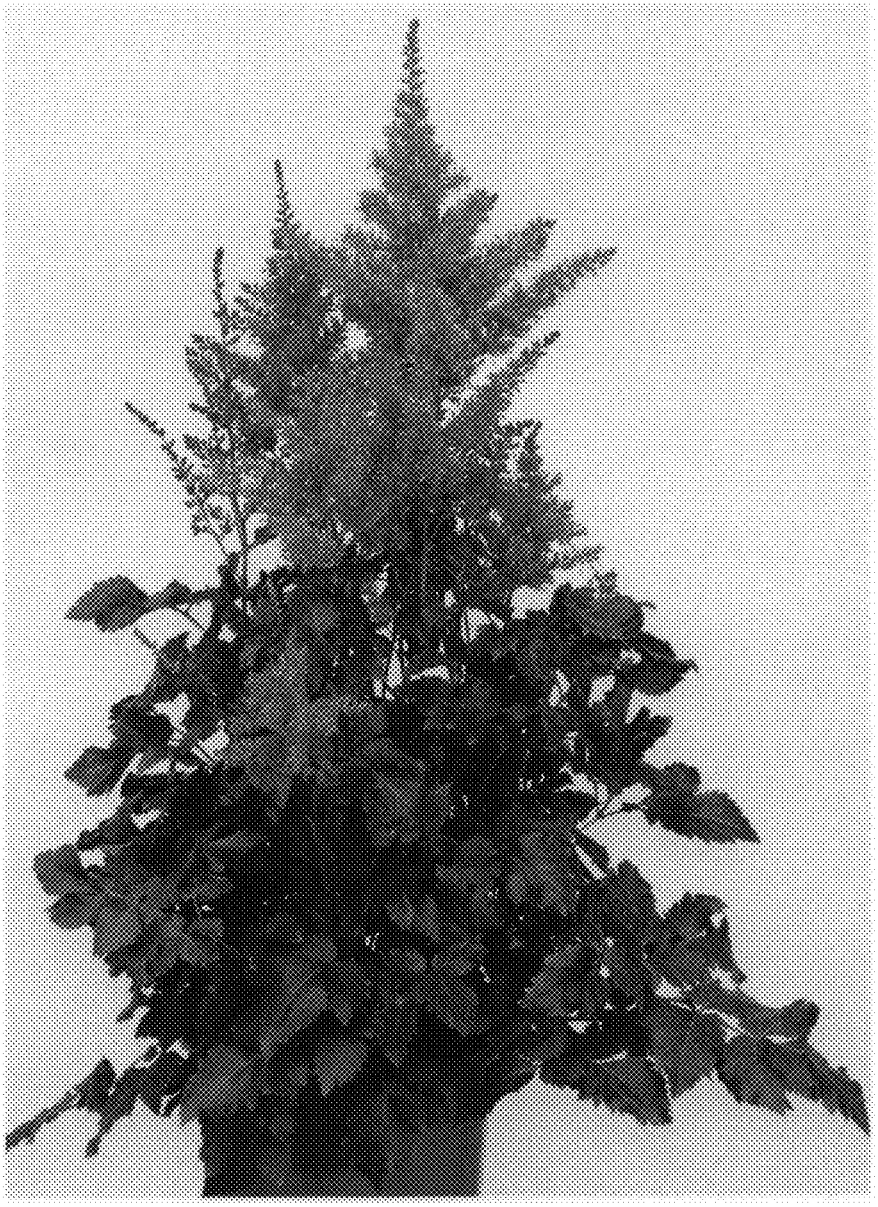

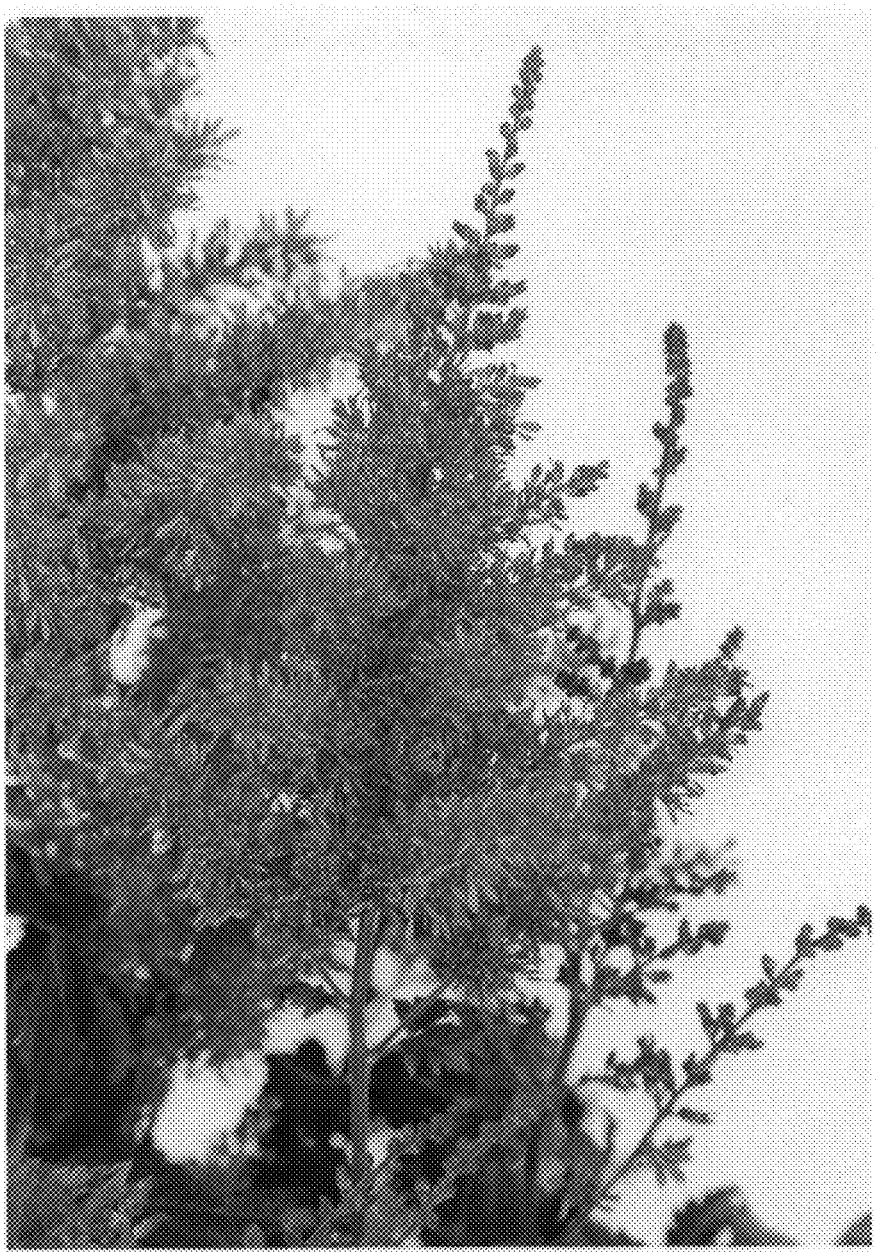

* * * * *